United States Patent
Muhs et al.

[11] Patent Number: 6,011,195
[45] Date of Patent: Jan. 4, 2000

[54] WET RESILIENT ABSORBENT ARTICLE

[75] Inventors: Laura Jane Muhs, Kiel; Rebecca Lyn Dilnik, Neenah; Duane Michael Guralski, Neenah; Mark Newland Parsons, Neenah, all of Wis.

[73] Assignee: Kimberly-Clark Worldwide, Inc., Neenah, Wis.

[21] Appl. No.: 08/720,959

[22] Filed: Oct. 10, 1996

[51] Int. Cl.[7] .............................. A61F 13/15; A61F 13/20
[52] U.S. Cl. .......................................... 604/367; 604/378
[58] Field of Search ................... 604/367–377, 604/378

[56] References Cited

U.S. PATENT DOCUMENTS

| | | |
|---|---|---|
| 810,122 | 1/1906 | Green . |
| 810,123 | 1/1906 | Green . |
| 810,125 | 1/1906 | Green . |
| 810,127 | 1/1906 | Green . |
| 810,130 | 1/1906 | Green . |
| 2,024,976 | 12/1935 | Mathey et al. ............................ 128/290 |
| 3,364,931 | 1/1968 | Hirsch ..................................... 128/290 |
| 3,592,194 | 7/1971 | Duncan ................................... 128/287 |
| 3,699,966 | 10/1972 | Chapuis .............................. 128/290 R |
| 3,749,627 | 7/1973 | Jones, Sr. ............................... 156/268 |
| 3,828,786 | 8/1974 | Cervantes .......................... 128/290 R |
| 3,897,784 | 8/1975 | Fitzgerald .......................... 128/290 R |
| 3,954,107 | 5/1976 | Chesky et al. ...................... 128/290 R |
| 4,029,101 | 6/1977 | Chesky et al. ...................... 128/290 R |
| 4,195,634 | 4/1980 | DiSalvo et al. ..................... 128/290 R |
| 4,333,463 | 6/1982 | Holtman ................................. 128/287 |
| 4,731,065 | 3/1988 | Yamada ................................... 604/355 |
| 4,834,735 | 5/1989 | Alemany et al. ........................ 604/368 |
| 4,988,344 | 1/1991 | Reising et al. .......................... 604/368 |
| 4,988,345 | 1/1991 | Reising ................................... 604/368 |
| 5,013,309 | 5/1991 | Baigas, Jr. et al. ..................... 604/368 |
| 5,047,023 | 9/1991 | Berg ....................................... 604/368 |
| 5,048,489 | 9/1991 | Fischer et al. .......................... 123/467 |
| 5,048,589 | 9/1991 | Cook et al. ............................. 162/109 |
| 5,062,840 | 11/1991 | Holt et al. ............................ 604/385.1 |
| 5,134,007 | 7/1992 | Reising et al. ............................ 428/78 |
| 5,176,672 | 1/1993 | Bruemmer et al. .................. 604/385.1 |
| 5,294,478 | 3/1994 | Wanek et al. ........................... 604/378 |
| 5,330,459 | 7/1994 | Lavon et al. ......................... 604/385.1 |
| 5,399,412 | 3/1995 | Sudall et al. ............................ 428/153 |
| 5,401,267 | 3/1995 | Couture-Dorschner et al. ....... 604/384 |
| 5,437,653 | 8/1995 | Gilman et al. .......................... 604/378 |
| 5,439,458 | 8/1995 | Noel et al. .............................. 604/378 |
| 5,451,442 | 9/1995 | Pieniak et al. ............................ 428/54 |

FOREIGN PATENT DOCUMENTS

| | | |
|---|---|---|
| 0 119 919 | 9/1984 | European Pat. Off. . |
| 0 165 807 A1 | 12/1985 | European Pat. Off. . |
| 0 335 253 A1 | 10/1989 | European Pat. Off. . |
| 0 343 941 A3 | 11/1989 | European Pat. Off. . |
| 0 422 504 A3 | 4/1991 | European Pat. Off. . |
| 0 572 033 A3 | 12/1993 | European Pat. Off. . |
| 2 133 987 | 8/1984 | United Kingdom . |
| WO 85/02110 | 5/1985 | WIPO . |
| WO 94/23761 | 10/1994 | WIPO . |
| WO 95/00095 | 1/1995 | WIPO . |

*Primary Examiner*—John G. Weiss
*Assistant Examiner*—Ki Yong O
*Attorney, Agent, or Firm*—Thomas D. Wilhelm; Brian R. Tumm; Mark L. Davis

[57] ABSTRACT

Disclosed is an absorbent article, such as a disposable diaper, incontinent pad, sanitary napkin and the like that has as a component of the absorbent core a fluff cellulosic material. The absorbent core is especially effective and efficient for absorbing body fluids contacting the surface of the absorbent article. The absorbent core comprises a first absorbent layer having a fluff cellulosic material and a second absorbent layer of a resilient cellulosic material. The first absorbent layer can have an acquisition orifice so the second absorbent layer can quickly acquire any discharged body fluids. The absorbent article exhibits excellent wet crush recovery substantially without the use of polymeric or polyolefinic materials in either of the absorbent layers. The absorbent core when laterally crushed to approximately 40% of its initial dimension will recover to at least about 70% of its initial, precrushed dimension.

35 Claims, 3 Drawing Sheets

WET RESILIENT ABSORBENT ARTICLE

FIELD OF THE INVENTION

This invention relates to a disposable absorbent article and particularly to a sanitary napkin having an improved absorbent core that effectively and efficiently acquires and distributes fluids absorbed therein. More specifically, the invention relates to a sanitary napkin having a multi-layered absorbent core with at least one of the layers having a resilient cellulosic material exhibiting excellent wet crush recovery.

BACKGROUND OF THE INVENTION

The present invention relates to disposable absorbent articles, such as diapers, sanitary napkins, training pants, incontinent garments, overnight pads, panty liners, underarm shields, as well as other absorbent devices used for medical purposes, such as, surgical absorbents which utilize, to some degree, fluffed wood pulp fibers. Such articles are designed to absorb body fluids, such as urine, menses, blood, perspiration and other excrement discharged by the body. In order for such absorbent articles to function efficiently, the absorbent core must quickly absorb into the structure body fluids insulting its surface, retain the body fluid within the absorbent core and prevent body fluids from being discharged onto the person and/or the wearer's adjacent clothing.

The basic form of the absorbent article is well known and typically includes a bodyside, liquid-permeable cover, a garment-side, liquid-impermeable baffle and an absorbent core positioned between the cover and the baffle. Numerous variations of the elements in addition to the basic cover, baffle and absorbent core arrangement are known. Each additional element is usually directed to improving a specific characteristic of the absorbent article. Generally, on the larger absorbent articles, i.e. those designed to absorb and retain at least 20 grams of fluid, such as diapers, training pants, incontinent garments, overnight pads and maxi sanitary napkins, the absorbent core incorporates an absorbent batt that is used to absorb and retain the body fluids. This batt, sometimes referred to as "wadding", is composed of one or more layers of fluffed wood pulp and typically has a substantial thickness, that is, greater than about 5 millimeters. Advantageously, the fluffed wood pulp layer is quite soft, flexible, and comfortable. However fluffed wood pulp has a disadvantage of poor in-plane wicking ability. Since the fluid to be absorbed is usually deposited in a localized area within the absorbent batt the fluff wood pulp does not efficiently transport body fluids for effective utilization of absorbent article absorbent capacity.

Another disadvantage of the fluffed wood pulp is that it has a low wet resiliency or a low wet stability. This allows the batt to collapse when wet, exacerbating low in plane fluid distribution, enhancing the probability that the absorbent article will sag, clump-up, bunch, twist or rope. To overcome these disadvantages it is known in the absorbent art to incorporate into a fluffed wood pulp batt a moisture stable material such as a polymeric material. Although these polymeric materials provide a wet stability to the batt they are generally hydrophobic. To obtain a satisfactory wet stability it usually requires a substantial amount of the polymeric material, relative to the amount of pulp, be incorporated into the batt which impedes the fluid distribution and capacity of the fluffed wood pulp batt.

Improving the performance of a disposable absorbent article which utilizes a fluffed wood pulp absorbent batt continues to be a formidable undertaking, although a number of improvements have been made in both the materials used and its construction. Improving fluid handling performance and wet resiliency protection without compromising comfort and fit has not yet met the desired needs of the consumer.

SUMMARY OF THE INVENTION

Briefly, this invention relates to an absorbent article having a liquid permeable cover, a liquid impermeable baffle and an absorbent core positioned between the cover and the baffle. The absorbent core has at least two layers of an absorbent material. The first absorbent layer comprises substantially a fluff wood pulp having an acquisition orifice therein. The acquisition orifice is configured to have a ratio of the length dimension to width dimension greater than unity. The second absorbent layer is one or more layers of a wet resilient, cellulosic material. This combination provides an absorbent article having greater absorbent utilization, is very comfortable and provides an absorbent core with an wet crush width recovery of greater than about 70 percent.

The general object of this invention is to provide an absorbent article having an absorbent core that is highly effective and efficient in rapidly acquiring and containing fluids. A more specific object of this invention is to provide a sanitary napkin having at least two absorbent layers with an acquisition orifice in the absorbent layer proximate the cover.

It is another object of the invention is to provide a sanitary napkin having a wet resilient, cellulosic absorbent material as that is especially effective in acquiring, distributing, and storing fluid insults.

Another object of the invention is to provide a sanitary napkin having an absorbent core with a width recovery of greater than about 70 percent when the absorbent core is loaded with 25 milliliters of water and laterally compressed to 40% of its preloaded and precrushed dimension.

DETAILED DESCRIPTION OF THE INVENTION

Figure 1:
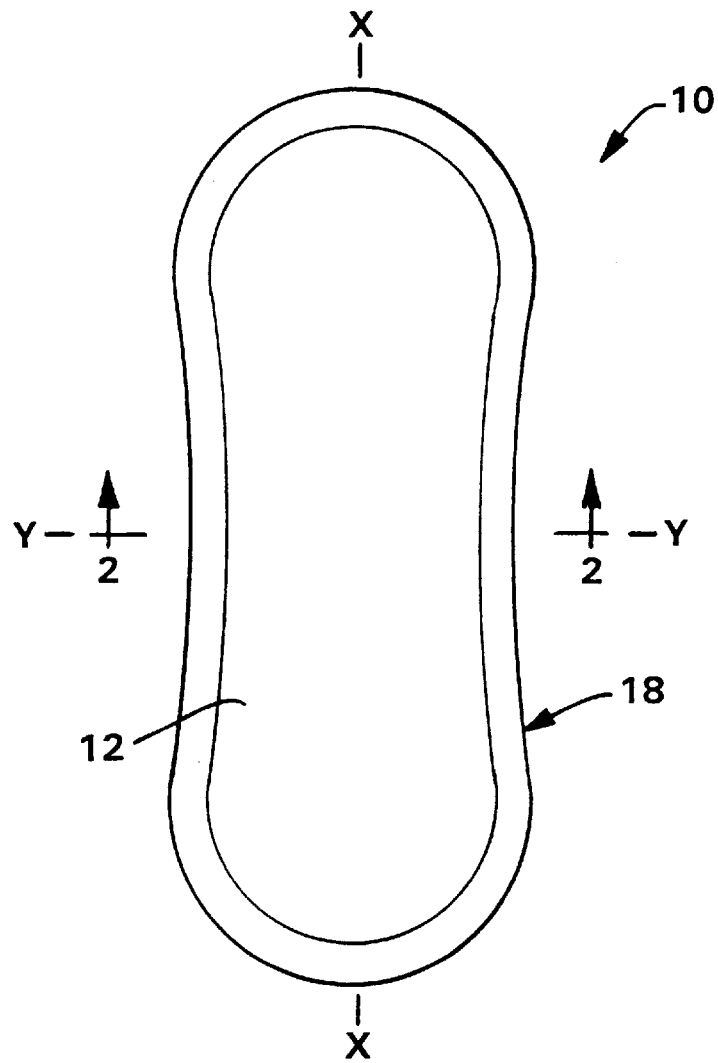
FIG. 1 is a top plan view of an absorbent article, illustrated as a sanitary napkin, having a multi-layered absorbent structure.
Figure 2:
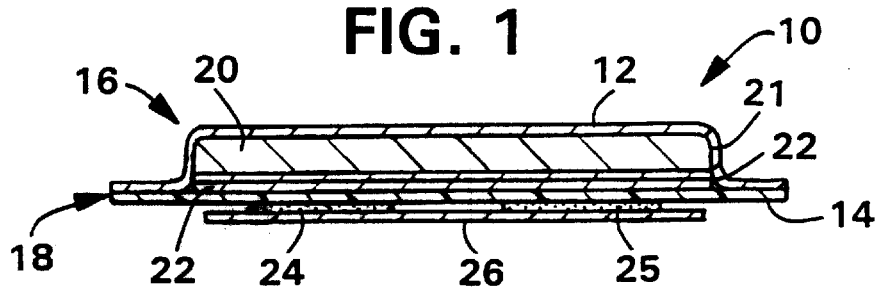
FIG. 2 is a cross-sectional view of the absorbent article taken along the transverse line 2—2 of FIG. 1.

Referring to the Figures, where like numerals indicate like parts throughout the several views and embodiments, in FIGS. 1 and 2, a disposable absorbent article 10 is depicted as a sanitary napkin. As used herein, the term "disposable absorbent article" refers to articles which absorb and retain body exudates and which are typically placed against or in proximity to the body of the wearer to absorb and contain various exudates discharged from the body, and which are intended to be discarded after a single use. A sanitary napkin is designed to be worn by a woman to absorb body fluids such as menses, blood, urine and other excrements. A sanitary napkin is also referred to as a catamenial pad or a feminine pad. Although the absorbent article 10 will be described with reference to a sanitary napkin, it can also encompass other articles such as an incontinent garment, incontinent shields, and the like which incorporate a fluffed wood pulp absorbent. Furthermore, the sanitary napkin 10 can be used either alone or in combination with underwear, menstrual panties, or specially designed belts, straps or harnesses.

The sanitary napkin 10 can include a liquid-permeable cover 12, a liquid-impermeable baffle 14 and an absorbent core 16 positioned between the cover 12 and the baffle 14. FIG. 1 shows a preferred embodiment of the sanitary napkin 10 in which the cover 12 and baffle 14 extend beyond the absorbent core 16 in a contiguous relationship and are sealed together to define a periphery 18 of the sanitary napkin 10. The cover 12 and the baffle 14 may be sealed together using any suitable means that will not leave a hard, uncomfortable residue that may be annoying to the wearer. As used herein, the term "sealed" encompasses configurations whereby the cover 12 is directly joined to baffle 14 and configurations whereby the cover 12 is indirectly joined to the baffle 14 by affixing each to an intermediate member. Methods for attaching the cover 12 and baffle 14 are well known to those skilled in the art and include the use of hot melt adhesives, pressure-sensitive adhesives, double-sided tape, sonic bonding, heat sealing and the like.

The sanitary napkin 10 includes a central longitudinal x-axis, denoted X--X, and a central transverse y-axis, denoted Y--Y. The transverse y-axis is perpendicularly orientated relative to the longitudinal x-axis. The sanitary napkin 10 has a length, measured along the longitudinal axis X--X, of between about 150 mm to about 300 mm and a width, measured along the transverse y-axis Y--Y, of between about 50 mm to about 125 mm. The sanitary napkin 10 generally has a hourglass shape but is not limited to this shape. Non-limiting examples of other shapes include rectangular, oval shape, dogbone, or racetrack.

Looking at the individual components in greater detail, the cover 12 is designed to contact the body of the wearer so should be soft feeling, compliant and non-irritating to the wearer's skin. The cover 12 should be liquid permeable and easily penetrated by body fluids. The cover 12 can be constructed from a woven or nonwoven material, porous foam, reticulated foam, finely-perforated film web, net materials, natural or synthetic fibers or combinations thereof. Suitable materials include, but are not limited to, bonded carded webs of cotton, polyester, polypropylene, polyethylene, and nylon. Other polyolefins, such as copolymers of polypropylene and polyethylene and linear low-density polyethylene also work well. A particular preferred material is a composite of an apertured thermoplastic film positioned above a nonwoven fabric material. Such composite material can be formed by extrusion of a polymer onto a web of spunbond material to form an integral sheet. One example of this is an apertured thermoplastic film bonded to a spunbond material. This material exhibits a smooth and soft outer surface which is not irritating to the wearer's skin and yet has a cushioned feel because of it's bulk.

Another preferred material for the cover 12 is a spunbond web of polypropylene. The web can contain from between about 1 percent to about 6 percent of titanium dioxide pigment to give it a clean, white appearance. A uniform thickness of spunbond is desirable because it will have sufficient strength, after being perforated in the longitudinal direction, to resist being torn or pulled apart during use. The most preferred polypropylene webs have a weight of between about 18 to about 40 grams per square meter. An optimum weight is between about 30 to about 40 grams per square meter.

The liquid-permeable cover 12 can also contain a plurality of apertures, not shown, formed therethrough. The apertures can be arranged uniformly or randomly over either the entire surface of the cover 12 or over a portion of the surface of the cover 12. For example, the apertures can be arranged in a band extending along the central longitudinal x-axis. The band of apertures can run the entire length of the sanitary napkin 10 or be present over only a portion of the overall length. The apertures are intended to facilitate the movement of body fluid which is deposited onto the cover 12 to penetrate down into the absorbent core 16.

Positioned distally from the cover 12 is the baffle 14. The baffle 14 is liquid-impermeable but may permit the passage of air or vapor out of the sanitary napkin 10 while blocking the passage of body fluid. The baffle 14 can be made from any material having these properties. The baffle 14 can also be constructed from a material that will block the passage of vapor as well as fluids, if desired. A good material for the baffle 14 is a micro-embossed, polymeric film, such as polyethylene or polypropylene. Bicomponent films can also be used. A preferred material is polyethylene film. Most preferably, the baffle 14 will be comprised of a polyethylene film having a thickness in the range of from about 0.5 mm to about 2.0 mm.

As is depicted in FIG. 1, the baffle 14 can be cut to a size and shape which will make it coextensive with the cover 12. When this is done, the cover 12 and the baffle 14 can be bonded in a face to face contact to form a peripheral sealed sanitary napkin. It is also possible to wrap the cover 12 completely around the absorbent 16 and then adhere the cover 12 to the upper surface of the baffle 14, not shown, producing what is known in the art as a wrapped pad. Alternatively, the baffle 14 can be wrapped up along the side edges of the absorbent 16 and then the cover 12 can be wrapped completely around both the baffle 14 and absorbent 16, also not shown. These and other variations are known to those skilled in the disposable absorbent article art.

Positioned between the cover 12 and the baffle 14 is the absorbent core 16. The absorbent core 16 is preferably flexible, compressible, conformable, non-irritating to the wearer's skin, capable of absorbing and retaining body fluids, and desirably is free of or void of any superabsorbent material. By "superabsorbent" it is meant those absorbent materials usually employed in sanitary napkins, diaper, training pants, etc. that are capable of absorbing and retaining fluid several times their own weight. Non-limiting examples of superabsorbents include hydroxy functional polymers, hydrogel-forming polymers, cross-linked copolymers, etc. Such superabsorbents are normally supplied by such companies as Dow Chemical, Hoechst-Celanese, and Stockhausen, Inc.

Figure 3:
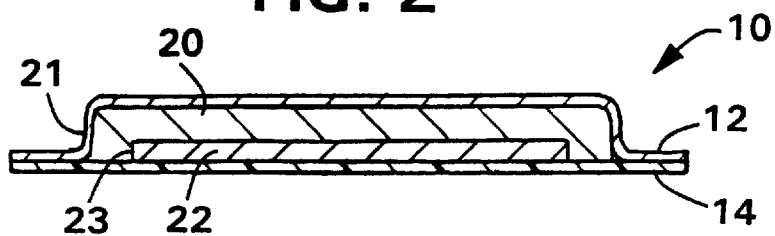
FIG. 3 is a cross-sectional view of another embodiment of the absorbent article taken along the transverse similar to line 2—2 of FIG. 1.

Referring to FIGS. 1–3, the absorbent core 16 is generally a multi-layered structure having a first absorbent layer 20 and a second absorbent layer 22. It should be understood that for purposes of this invention the absorbent core 16 is not limited to single layers or sheets of material. It is quite possible for the first and second absorbent layers 20 and 22 to be constructed from laminates or combinations of several sheets or webs of the requisite type of materials as described below. Thus, as used herein, the term "layer" includes the singular and plural use of the word. The first absorbent layer 20 is desirably positioned adjacent to and is in liquid communication with at least a portion of the cover 12. The first absorbent layer 20 and second absorbent layer 22 have an outer boundary 21 and 23, respectively. Desirably, the outer boundaries 21 and 23 are coextensive. Alternatively, the first absorbent layer 20 can have a length and width dimension greater than that of the second absorbent layer 22 so that the outer boundary 21 of the first absorbent layer 20 extends beyond and projects over the outer boundary 23 of the second absorbent layer 22, as seen in FIG. 3.

The first absorbent layer 20 is constructed from a material that consists substantially of hydrophilic wood pulp fibers, also known as a fluff wood pulp and has a caliper or thickness of less than about 3 millimeters. As discussed above, it is known in the art that such fluff wood pulp exhibits excellent fluid wettability but is not wet stable. The present invention provides an absorbent article utilizing the advantage of a wood fluff pulp and increases the wet stability of the fluff wood pulp. Desirably, the fluff wood pulp contains less than 10% by weight of a polymeric composition and preferably, the fluff wood pulp is void of any material, such as a polyolefinic or polymeric composition, that would substantially change the wettability and fluid distribution through the fluff wood pulp having a similar basis weight or density. The first absorbent layer 20 can have a density ranging from about 0.03 grams per cubic centimeter ($g/cm^3$) to about 0.25 $g/cm^3$. Desirably, the first absorbent layer 20 has a density ranging from about 0.05 $g/cm^3$ to about 0.2 $g/cm^3$.

The second absorbent layer 22, which preferably is flexible and resilient, is positioned between the baffle 14 and the first absorbent layer 20. The second absorbent layer 22 is substantially a cellulosic material and preferably, is an uncreped through air dried sheet of cellulosic material (UCTAD) that is void of any polymeric or polyolefinic materials that would substantially change the character of the cellulosic material. The UCTAD material is described in greater detail in U.S. Pat. Nos. 5,048,589 and 5,399,412 both commonly assigned to Kimberly-Clark Corporation, the entire contents of both being incorporated herein by reference and made a part hereof. Since the second absorbent layer is formed from one or more flat, resilient sheets of absorbent UCTAD layers it is excellent in flexibility and can be appropriately deformed without acquiring a bunched, twisted or roped configuration during use or after a fluid insult. Alternatively, the second absorbent layer can be made from one sheet of material that is adequately dimensioned to be folded to effectively acquire a multi-layer configuration. Non-limiting examples of this would be an e-fold where one sheet is trifolded, an accordion fold, or zigzagging a sheet of material back and forth to the desired width dimension.

The sanitary napkin 10 also includes two elongated strips 24 and 25 of garment adhesive which are secured to the bottom of the baffle 14. The adhesive strips 24 and 25 are spaced apart and function to attach the sanitary napkin 10 to the inner crotch portion of an undergarment during use. The garment adhesive 24 and 25 enable the sanitary napkin 10 to be properly aligned and retained relative to the user's vaginal opening so that maximum fluid protection can be obtained.

It should be noted that the two strips of garment adhesive 24 and 25 could be replaced with a single strip if desired. Alternatively, a swirl pattern of adhesive or some other type of adhesive pattern can also be used. The garment adhesive is of such a nature that it will allow the user to remove the sanitary napkin 10 and reposition it on her undergarment if needed. The garment adhesive is commercially available from National Starch and Chemical Company having an office located at 10 Findeme Avenue, Bridgewater, N.J. 08807.

A releasable peel paper 26 protects the two garment adhesive strips 24 and 25 from contamination prior to use. The peel paper 26 can be a white Kraft paper coated on one side so that it can be released from a hot melt adhesive. The peel paper is designed to be removed by the user immediately before she attaches the sanitary napkin 10 onto the inner crotch portion of her undergarment.

The sanitary napkin 10 of the present invention generally has a caliper or thickness greater than about 5 millimeters. The caliper of the sanitary napkin 10 is measured without the peel strip 26 and with the adhesive 24 and 25 blocked using talc or cornstarch. The caliper of the sanitary napkin 10 is determined by placing a Lucite block, measuring 12.7 mm by 44.5 mm (0.5 of an inch by 1.75 inches) on top of the sanitary napkin 10. The thickness is determined with an indicator gauge that measures the distance of the block above a flat surface. The block is placed with one of the 44.5 mm (about 1.75 inch) long edges along one of the long edges of the absorbent core 16 with all of the block itself being on top of the absorbent core 16. The block is roughly centered along the length of the sanitary napkin 10. The height of the sanitary napkin 10 plus the block, is then subtracted from the height of the block alone on the surface, to give the thickness or caliper of the sanitary napkin 10.

Figure 5:
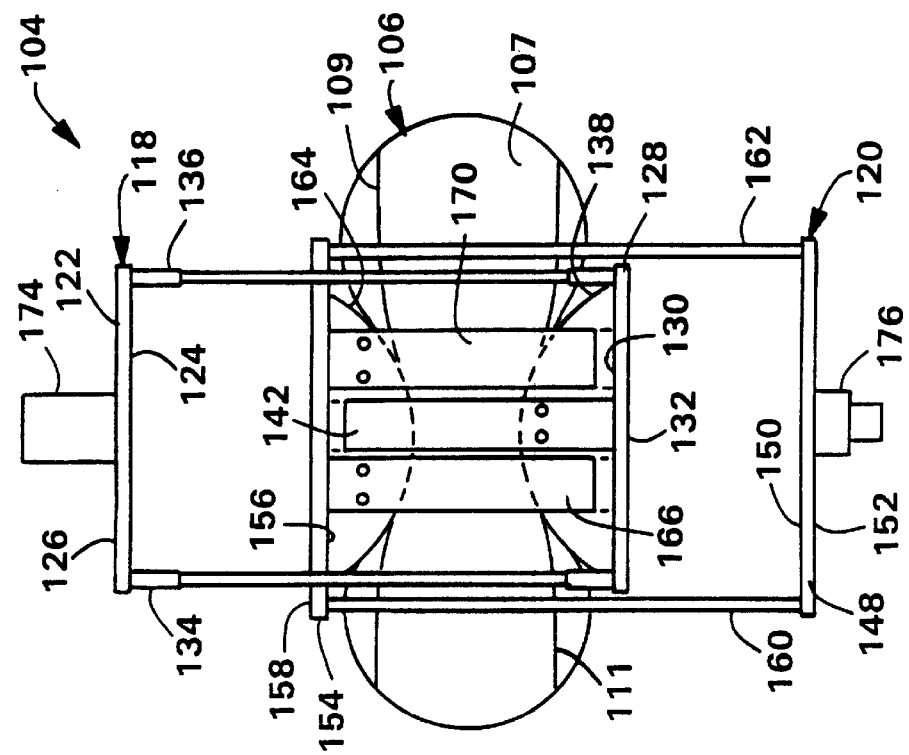
FIG. 5 is a front elevational view of the apparatus in a closed position depicting the absorbent article having been crushed sideways between first and second frame members.
Figure 4:
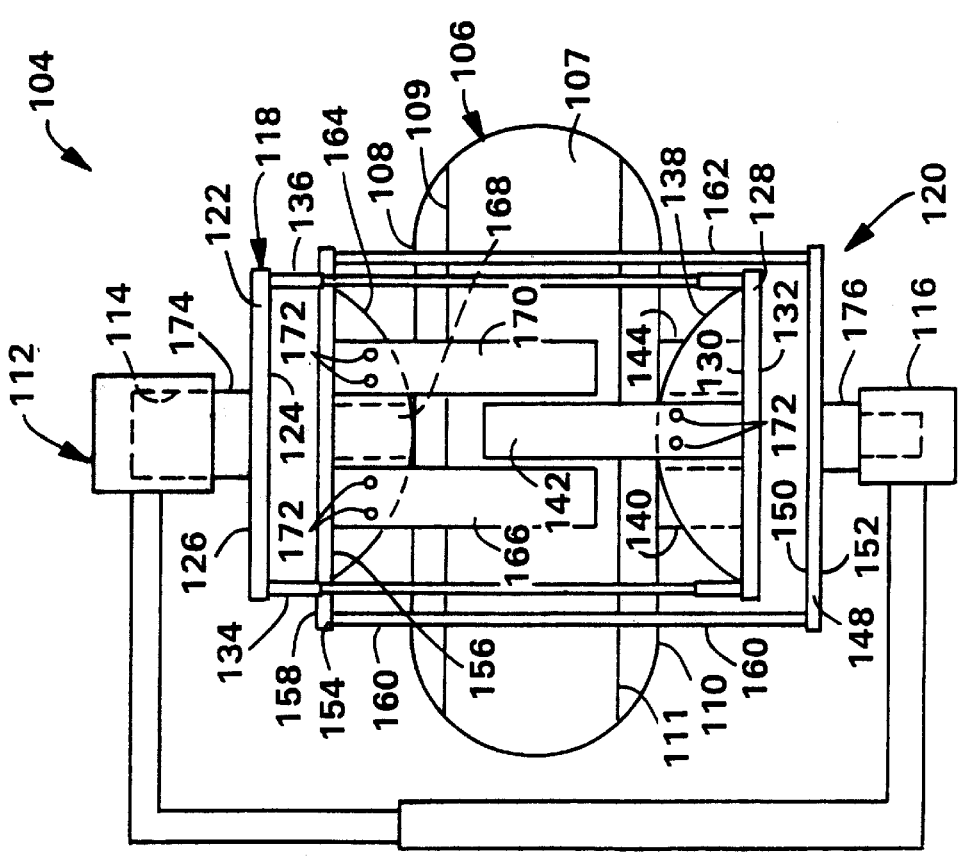
FIG. 4 is a front elevational view of an apparatus in an open position depicting a non-crushed absorbent article positioned between first and second frame members and attached to a tester.

The absorbent core 16 of the present invention must be resilient when wet so that when a lateral compressive force, or crushing force, is removed the sanitary napkin 10 will substantially return to its original size and shape. For the purpose of the present invention, resiliency is determined by the wet crush width recovery of the absorbent core 16. Desirably, the absorbent core 16 has a wet crush width recovery greater than about 70 percent, preferably, the absorbent core 16 has a wet crush width recovery greater than about 80 percent, and more preferably, the absorbent core 16 has a wet crush width recovery greater than about 90 percent. Referring to FIGS. 4 and 5, the wet crush recovery value is determined according to the procedure below.

All of the absorbent articles to be tested should be acclimated for at least two hours in a controlled environment at a temperature of 23° C.+1° C. (73.4° F.+1.8° F.) and a relative humidity of 50+2 percent.

The "wet crush width recovery" value is measured using an apparatus 104 depicted in FIGS. 4 and 5. The apparatus 104 is designed to retain an absorbent article 106 having a pair of spaced apart longitudinal side edges 108 and 110. The absorbent article 106 also has an absorbent 107 with a pair of spaced apart longitudinal side edges 109 and 111. The side edges 109 and 111 can be coincidental with or spaced inward from the longitudinal side edges 108 and 110 of the absorbent article 106.

Referring to FIG. 4, a tester 112 is depicted which is capable of measuring the force, in grams, required to crush the absorbent article 106 sideways. By sideways is meant along the transverse central y-axis which is shown in FIG. 1. The tester 112 includes first and second arms, 114 and 116 respectively, only one of which has to be movable. The first and second arms 114 and 116 are coaxially aligned and spaced apart. The distance to which the arms 114 and 116 are separated can be varied to accommodate the size of the apparatus 104 and the size of the absorbent article 106 which is to be tested. The tester 112 is capable of moving at least one of the arms 114 and/or 116 relative to the other arm at a predetermined speed. One common tester which can be used is a Sintech® 1/S which is available from Sintech, a division of MTS Systems Corp. having an office at 1400 Technology Drive, Eden Prairie, Minn. 55344. A commercially available, alternative tester is an Instron® tester available from Instron Corporation having an office at 100 Royall Street, Canton, Mass. 02021.

The apparatus 104 includes a first frame member 118 and a second frame member 120 which are interleaved to operate in unison. The first frame member 118 and a second frame member 120 are reciprocally movable relative to one another. Both of the frame members, 118 and 120 respectively, can be rectangular in configuration. Other shapes may work equally as well. The first frame member 118 has a first plate 122 with an inner surface 124 and an outer surface 126. The first frame member 118 also has a second plate 128 with an inner surface 130 and an outer surface 132. The first and second plates, 122 and 128 respectively, are joined together by at least two support members 134 and 136, and preferably, by four support members.

In FIGS. 4 and 5, four support members are actually present but only the two support members, 134 and 136 respectively, are visible. The remaining two support members are located directly behind and at a distance from the two support members 134 and 136. When four support members are present, they can be arranged in a rectangular fashion such that each is connected to a corner of the first and second plates, 122 and 128 respectively.

Secured to or formed on the inner surface 130 of the second plate 128 is a shoulder 138. The shoulder 138 can have an arcuate shape and more preferably a semi-circular configuration having a radius of about 76 millimeters (about 3 inches). The semi-circular configuration of the shoulder 138 should have a smooth profile which contacts the central section of the longitudinal side edge 110 of the absorbent article 106. The shoulder 138 should have a fixed width depending upon the thickness of the absorbent article 106. The width of the shoulder 138 is measured along a line extending perpendicular to the plane of the sheet illustrated in FIG. 4. The shoulder 138 should have a width of about 11 mm for an absorbent article which has a thickness or caliper ranging from between about 2 mm to about 7 mm. The shoulder 138 should have a width or thickness of about 17 mm. A method of measuring the thickness of an absorbent article 106 is described above.

Extending outwardly from the shoulder 138 is at least one, preferably two, and more preferably three or more wands 140, 142 and 144. Each wand 140, 142, and 144 can be secured to the shoulder 138 and/or to the second plate 128 by a common fastener, for example by a pair of screws 172, as shown. Other fasteners, such as bolts, nuts, rivets, pins, etc. can also be used, as well as attachment by welding, fusion, adhesive, etc. These and other methods of attaching or securing the wands 140, 142 and 144 to the shoulder 138 and/or the first plate 122 are known to those skilled in the art.

The wands 140, 142 and 144 should be flexible members so as to be capable of bending outwardly as the absorbent article 106 gets thicker as it is crushed along the y-axis. The wands 140, 142 and 144 can be constructed of a pliable or bendable material such as plastic or rubber or they can be made from thin pieces of metal, wood, etc. For measuring the "wet crush recovery" value of a thin absorbent article, like a sanitary napkin, each wand 140, 142 and 144 can be a thin plastic strip having a length of about 89 mm (about 3.5 inches), a width of about 19 mm (about ¾ of an inch) and a thickness of about 1.6 mm (about 1/16 of an inch). The exact dimension can vary to suit one's particular absorbent article. Each wand 140, 142 and 144 extends outwardly toward the first plate 122. The wands 140, 142 and 144 can be oriented parallel to one another and can be spaced apart so as not to interfere with one another. In FIGS. 4 and 5, the wands 140 and 144 are secured to one side of the shoulder 138 while the wand 142 is secured to the opposite side of the shoulder 138. This allows the wands 140, 142 and 144 to be offset from one another.

The second frame member 120 can be constructed to be very similar to or identical in configuration to the first frame member 118 except that it will have to be of a slightly different size so as to permit the two frame members 118 and 120 to be interleaved. By "interleaved" is meant that the first frame member 118 is assembled in such a fashion with the second frame member 120 that one can move relative to the other while being separated therefrom. The second frame member 120 has a third plate 148 with an inner surface 150 and an outer surface 152. The second frame member 120 also has a fourth plate 154 with an inner surface 156 and an outer surface 158. The third and fourth plates, 148 and 154 respectively, are joined together by at least two support members 160 and 162, and preferably, by four support members. The fourth plate 154 is so sized and shaped so as to be able to slide between the first and second plates, 122 and 128 respectively, of the first frame member 118.

In FIGS. 4 and 5, four support members are actually present but only the two support members 160 and 162 are visible. The remaining two support members are located directly behind the two support members 160 and 162. When four support members are present, they can be arranged in a rectangular fashion such that each is connected to a corner of the third and fourth plates, 148 and 154 respectively.

Secured to or formed on the inner surface 156 of the fourth plate 154 is a shoulder 164. The shoulder 164 can be arcuate in shape. More preferably, the shoulder 164 can have a semi-circular configuration, and should have a width identical to that described above for the shoulder 138. Extending outwardly from the shoulder 164 is at least one, preferably two, and more preferably three or more wands 166, 168 and 170. Each wand 166, 168, and 170 can be secured to the shoulder 164 and/or to the fourth plate 154 by a common fastener, for example a pair of screws 172, as shown. Other fasteners, such as bolts, nuts, rivets, pins, etc. can also be used, as well as attachment by welding, fusion, adhesive, etc. These and other methods of attaching or securing the wands 166, 168 and 170 to the shoulder 164 and/or the fourth plate 154 are known to those skilled in the art.

The wands 166, 168 and 170 can be similar or identical to the wands 140, 142 and 144 discussed above. Each of wands 166, 168 and 170 extends outwardly toward the third plate 148. The wands 166, 168 and 170 can be oriented parallel to one another and can be spaced apart so as not to interfere with one another. In FIGS. 4 and 5, the wands 166 and 170 are secured to one side of the shoulder 164 while the wand 168 is secured to the opposite side of the shoulder 164. This allows the wands 166, 168 and 170 to be offset from one another.

The wands 140, 142 and 144 secured to the first frame member 118 intermesh with but do not physically contact the wands 166, 168 and 170 secured to the second frame member 120. However, actual rubbing contact between the wands 140, 142, 144, 166, 168 and 170 can occur if desired, but is not viewed to be advantageous. When the wands 140, 142 and 144 engage or intermesh with the wands 166, 168 and 170, in a similar fashion as when the fingers on a person right and left hands come together, an opening or defined area is formed into which the absorbent article 106 can be inserted. The absorbent article 106 is positioned between the first and second frame members, 118 and 120 respectively. In this position, the wands 140, 142, 144, 166, 168 and 170 are aligned parallel to one another with the wands 140 and 144 offset from wand 168 while wands 166 and 170 are offset from wand 168. With the wands 140, 142, 144, 166, 168 and 170 engaged, there will be three wands located on each side of the absorbent article 106.

The first frame member 118 further has an attachment mechanism 174, such as an outwardly extending shaft, secured to the outer surface 132 of the first plate 122. The shaft 174 can be releasably attached to the first arm 114 of the tester 112. Likewise, the second frame member 120 has an attachment mechanism 176, such as an outwardly extending shaft, secured to the outer surface 152 of the third plate 148. The shaft 176 can be releaseably attached to the second arm 116 of the tester 112. With the apparatus 104 secured to the tester 112, movement of at least one of the arms 114 and 116 away from the other will cause the first frame member 118 to move relative to the second frame member 120. This will cause the two shoulders 138 and 164 to approach one another and squeeze the longitudinal side edges 108 and 110 of the absorbent article 106 thereby crushing the article 106 to a preselected distance between the shoulders 138 and 164.

The method of operating the apparatus 104 to determine the wet crush recovery of an absorbent article 106 sideways along the y-axis is as follows:

First, the apparatus 104 is secured in the tester 112, preferably in a vertical orientation. When secured, the first and second frame members, 118 and 120 respectively, of the apparatus 104 are attached to the two arms 114 and 116 of the tester 112. The first and second frame members, 118 and 120 respectively, are adjusted to be a predetermined distance apart, for example 102 mm (about 4 inches). This setting allows the absorbent article 106 to be positioned between the first and second frame members, 118 and 120 respectively, while still in a planar or non-buckled condition. A pre-calibrated load cell, for example, a 50 pound full scale, tension/compression load cell, is utilized.

Second, any wings, flaps, panels, tabs or appendages which may be attached to or integrally formed with the absorbent article 106 should be removed before the absorbent article 106 is tested. Such laterally extending wings, flaps, panels, tabs or appendages can be removed prior to testing, by cutting them off along a line approximately parallel to the longitudinal side edges 108 and 110 of the absorbent article 106.

Third, the peel strip should be removed and the garment adhesive should be blocked using cornstarch or talc.

Fourth, the width of the absorbent 107 is measured then the absorbent is wetted with 25 milliliters (ml) of 0.9 percent by weight saline or alternatively, water. This can be done by pouring the saline onto the center of the bodyside surface of the absorbent article 106 at a rate slow enough to allow all of the saline to be absorbed by the article 106.

Fifth, within 5 minutes after the initial insult, the wetted absorbent article 106 is then centered in the apparatus 104 as indicated in FIG. 4.

Sixth, the load cell of the tester 112 is zeroed per the manufacturer's instructions.

Seventh, the tester is then actuated causing the arms 114 and 116 to be separated, causing the longitudinal side edges 108 and 110 of the absorbent article 106 to be crushed toward one another between the shoulders 138 and 164. The crushing force is applied to the sanitary napkin 106 until the width of the absorbent 107, at its closest point, is approximately 40% of the original, pre-crushed dimensional value.

After the absorbent article 106 has been crushed, the arms 114 and 116 of the tester 112 are retracted to their original pretest position. In this position, the longitudinal side edge 110 of the absorbent article 106 is contacting the first shoulder 138 and the opposite longitudinal side edge 108 is spaced apart from the second shoulder 164. This arrangement allows the absorbent article 106 to freely recover toward its original transverse dimension. After approximately 30 seconds, the recovered width of the absorbent 107 is measured in millimeters. The recovered width is the distance between the longitudinal side edges 109 and 111 of the absorbent 107. The "wet crush recovery" value is this measured recovered width divided by the original pre-crushed width multiplied by 100%. This can be represented by the formula:

$$\frac{\text{wet crush recovery width}}{\text{Pre-crushed width of absorbent}} \times 100\%$$

Figure 6:
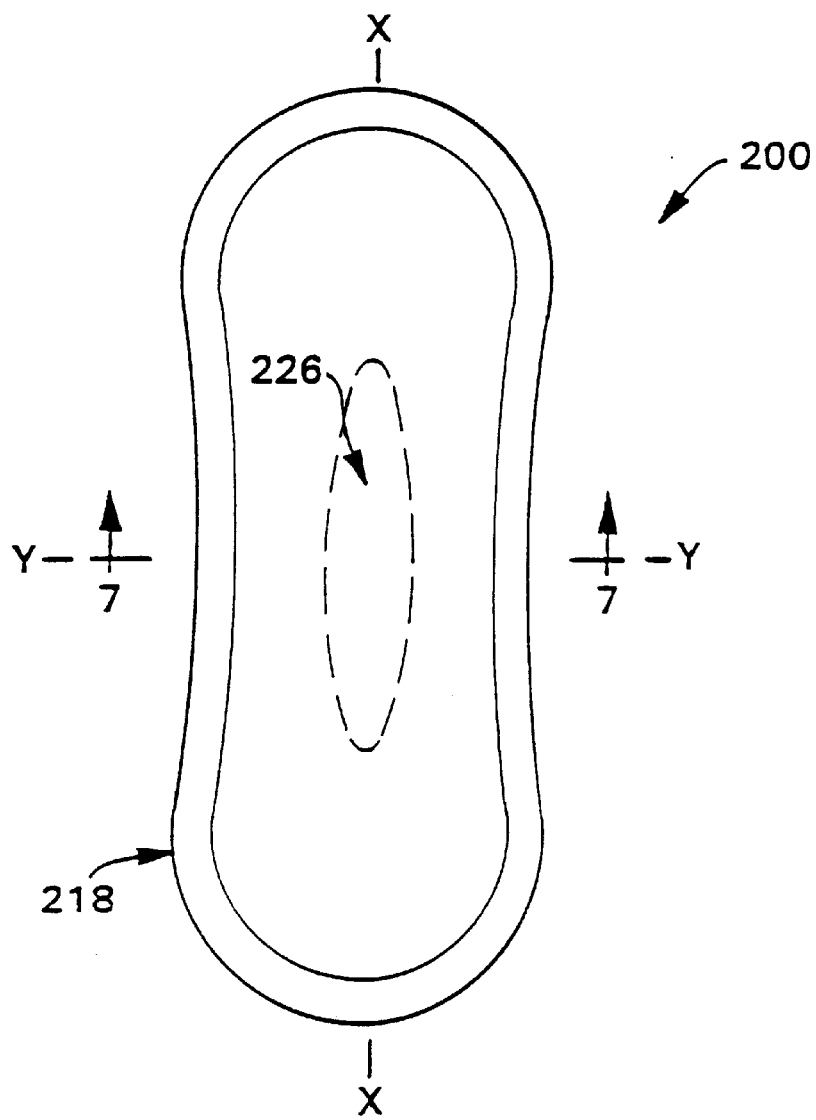
FIG. 6 is a top plan view of another embodiment of the invention illustrating an acquisition orifice in the top most absorbent layer for rapid fluid acquisition.
Figure 7:
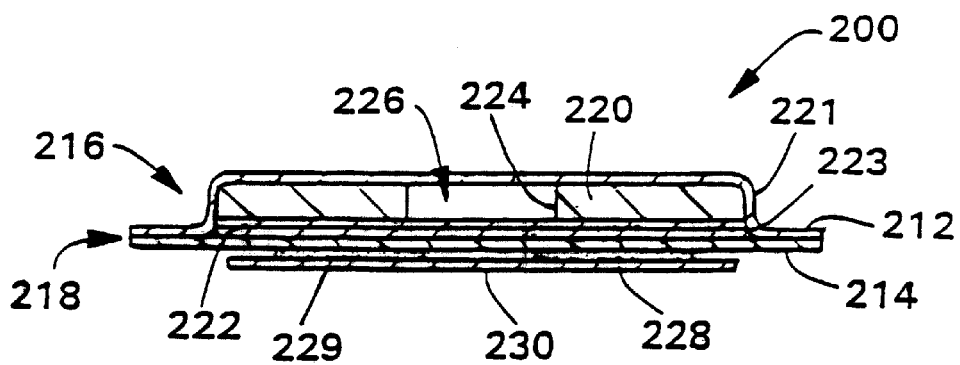
FIG. 7 is a cross-sectional view of the absorbent article taken along line 7—7 of FIG. 6.

Referring to FIGS. 6 and 7, another embodiment of an absorbent article is shown illustrated as a sanitary napkin 200. The sanitary napkin 200 includes a liquid-permeable cover 212, a liquid impermeable baffle 214 and an absorbent core 216. The cover 212, baffle 214 and absorbent core 216 are the same as described above in FIGS. 1–3. The cover 212 and baffle 214 extend beyond the absorbent core 216 in a contiguous relationship and are sealed together to define a periphery 218 of the sanitary napkin 200. The absorbent core 216 is generally a multi-layered structure having a first absorbent layer 220 and a second absorbent layer 222. The absorbent core 216 has a wet crush recovery value, as described above, greater than about 70%, preferably greater than 80% and more preferably, greater than 90%. The first and second absorbent layers 220 and 222 generally have an hourglass shape configuration with coterminous outer boundaries 221 and 223, respectively.

The first absorbent layer 220 includes an inner boundary 224 defining an acquisition orifice 226. The acquisition orifice 226 extends through the first absorbent layer 220 allowing the second absorbent layer 222 to be in direct liquid communication with the cover 212 so that liquids deposited on the cover 212 will be quickly acquired into the second absorbent layer 222. The cover 212 can be joined to the second absorbent layer 222 through the acquisition orifice 226 by use of an adhesive or other attachment means (not shown). Since the first absorbent layer comprises fluff wood pulp having a thickness generally less than about 3 millimeters, the cover 212 does not need to be attached to the second absorbent layer 222 to provide rapid liquid acquisition by the second absorbent layer 222. The acquisition orifice 226 provides a means through which liquids contacting the cover 212 can migrate down through the acquisition orifice 226 to the second absorbent layer 222 more quickly and will have a reduced tendency to pool on the surface of the cover 212. The acquisition orifice 226 serves to collect and to distribute to the second absorbent layer 222 substantial amounts of discharged liquid. Such liquids can generally be discharged in gushes or slowly over long periods of time. Accordingly, the acquisition orifice 226 must be able to quickly acquire and transport liquid from the point of liquid contact to other parts of the absorbent core 216 and preferably to the second absorbent layer 222.

The shape, size and position of the acquisition orifice 226 is important to the effectiveness of absorbent core 216 rapidly acquiring discharged liquids. In accordance with the present invention, the acquisition orifice 226 has a length, measured along the longitudinal axis X--X, and a width, measured along the transverse axis Y--Y, such that the ratio of the length to the width is greater than one. Desirably, the ratio of length to width is greater than about 2 and preferably, the ratio of length to width is greater than about 4. The acquisition orifice 226 is placed on the sanitary napkin substantially at the location or in the vicinity of the point of discharge of liquids so that it is capable of quickly acquiring such liquids at their contact zone. In a preferred embodiment illustrated in FIGS. 6 and 7, the acquisition orifice 226 is medially aligned along both the x-axis and the y-axis.

The size of the acquisition orifice 226 can generally be expressed as a percentage of the top surface area of the first absorbent layer 220 since this actually defines the initial area available for liquid absorption. In accordance with the present invention, the top surface of the acquisition orifice 226 preferably comprises less than about 50% of the total top surface area of the first absorbent layer 220. The "total top surface area" of the first absorbent layer 220 is measured as if the acquisition orifice 226 were not present and the first absorbent layer 220 is similar to that illustrated in FIGS. 1–3. More preferably, the top surface area of the acquisition orifice 226 comprises less than about 40% of the total top surface area of the first absorbent layer 220, with less than about 25% being most preferred. The acquisition orifice 226 can be any desired shape consistent with the absorbent requirement of the absorbent core 216 and meeting the requirements regarding the ratio of length to width delineated above. For example, the acquisition orifice 226 can be rectangular, oblong, hourglass shaped, dogbone shaped or elliptical. It is also understood that the acquisition orifice 226 can be a plurality of smaller orifices positioned so that at least a portion of the total surface area of the orifice is placed in the vicinity of the point of discharge of liquids so as to be capable of quickly acquiring such liquids at their contact zone (not shown).

The sanitary napkin 200 also includes two elongated strips 228 and 229 of garment adhesive similar to that described above for garment adhesive 24 and 25. A releasable peel paper 230 protects the two garment adhesive strips 228 and 229 from contamination prior to use. The peel paper is similar to that described above for the peel strip 26.

Comparative Examples 1–5

Values for the wet crush recovery of various sanitary napkins having a caliper greater than 5 millimeters were tested as described above. The results appear in Table I below.

TABLE I

| Products | Caliper | Initial Width | WRV |
| --- | --- | --- | --- |
| NF Maxi[1] | 11.6 | 60 | 57% |

TABLE I-continued

| Products | Caliper | Initial Width | WRV |
| --- | --- | --- | --- |
| KOTEX ® Maxi[2] | 13.4 | 60 | 57% |
| Always Ultra[3] | 14.2 | 60 | 55% |
| Always Compact[4] | 9.2 | 55 | 69% |
| SureFit Maxi[5] | 12.6 | 45 | 60% |

[1]New Freedom ® Maxi available from Kimberly-Clark Corporation.
[2]KOTEX ® Maxi available from Kimberly-Clark Corporation.
[3]Always Ultra available from Procter & Gamble Company.
[4]Always Compact available from Procter & Gamble Company.
[5]Stayfree ® SureFit Maxi with stayput wings available from Personal Products Company, a division of McNeil-PPC.

Examples 6–9

Two sanitary napkins were constructed in accordance with the present invention. Codes S and T each had a cover, 470 gsm embossed fluff wood pulp first absorbent layer having a medially positioned, elliptical acquisition orifice with a length of 100 cm and a width of 25 cm. The second absorbent layer was composed of 6 layers of 35 gsm of an UCTAD material. The baffle was a 1 mil polyethylene film material. Two lines of garment adhesive were on the garment side of the baffle which were blocked with cornstarch for the purpose of determining the wet crush recovery according to the procedure set forth above.

The wet crush recovery values for these sanitary napkins are given in Table II below.

TABLE I

| Products | Caliper | Initial Width | WRV |
| --- | --- | --- | --- |
| Code S | 7.7 | 61 | 97% |
| Code T | 8.2 | 60 | 97% |

From the data, it is clear that absorbent article having a fluff wood pulp as at least one of the absorbent layers and constructed in accordance with the present invention exhibits superior wet crush strength when compared to other absorbent articles known in the art.

While the invention has been described with reference to a preferred embodiment and illustrated with regard to a range of optional features, those skilled in the art will appreciate that various substitutions, omissions, changes and modifications may be made without departing from the spirit hereof. Accordingly, it is intended that the foregoing description be deemed merely exemplary of the preferred scope of the present invention and not be deemed a limitation thereof.

We claim:

1. An absorbent articles, comprising:
   a) a liquid permeable cover;
   b) a liquid impermeable baffle;
   c) an absorbent core positioned between said cover and said baffle, said absorbent core having a first absorbent layer and a second absorbent layer, said first absorbent layer substantially comprising a fluff wood pulp with an inner boundary defining an acquisition orifice, said acquisition orifice having a ratio of length to width greater than unity, said second absorbent layer consisting essentially of a resilient cellulosic material, said second absorbent layer providing said absorbent article with greater wet crush width recovery than a corresponding such absorbent article devoid of said resilient cellulosic material.

2. The absorbent article of claim 1 wherein said first absorbent layer has a first outer boundary and said second absorbent layer has a second outer boundary.

3. The absorbent article of claim 2 wherein said first and second outer boundaries are coextensive.

4. The absorbent article of claim 2 wherein said first outer boundary extends beyond said second outer boundary.

5. The absorbent article of claim 1 wherein said first absorbent layer incorporates less than 10% of a polymeric material into said fluff wood pulp.

6. The absorbent article of claim 1 wherein said first absorbent layer consists essentially of a fluff wood pulp.

7. The absorbent article of claim 1 wherein said first absorbent layer has a density ranging from about 0.03 g/cc to about 0.25 g/cc.

8. The absorbent article of claim 1 wherein said first absorbent layer has a density ranging from about 0.05 g/cc to about 0.2 g/cc.

9. The absorbent article of claim 7 wherein said absorbent article has a caliper greater than 5 millimeters and said first absorbent layer has a caliper of less than about 3 millimeters.

10. The absorbent article of claim 1 wherein said cover and said baffle extend beyond said absorbent core to form a periphery of said absorbent article.

11. The absorbent article of claim 1 wherein said acquisition orifice ratio is greater than 2.

12. The absorbent article of claim 1 wherein said acquisition orifice ratio is greater than about 4.

13. The absorbent article of claim 1 wherein said second absorbent layer is an uncreped through air dried cellulosic sheet.

14. An absorbent article as in claim 1, said absorbent article, when crushed so that said absorbent article is approximately 40% of the pre-crushed dimensional width of said absorbent article, having a wet crush width recovery of greater than about 70 percent of the pre-crushed dimensional width of said absorbent article approximately 30 seconds after being allowed to recover.

15. A sanitary napkin, comprising:
    a) a liquid permeable cover;
    b) a liquid impermeable baffle;
    c) an absorbent core positioned between said cover and said baffle, said absorbent core having a first absorbent layer and a second absorbent layer, said first absorbent layer substantially comprising a fluff wood pulp having less than about 10% of a polymeric material incorporated therewith, said first absorbent layer having an inner boundary defining an acquisition orifice, said acquisition orifice having a ratio of length to width greater than unity, said second absorbent layer consisting essentially of a resilient cellulosic material,
said sanitary napkin, when crushed so that said sanitary napkin is approximately 40% of the pre-crushed dimensional width of said sanitary napkin having a wet crush width recovery of greater than about 70 percent of the pre-crushed dimensional width of said sanitary napkin approximately 30 seconds after being allowed to recover.

16. A sanitary napkin as in claim 15, said acquisition orifice having a ratio of length to width greater than unity.

17. A sanitary napkin as in claim 15, said first absorbent layer comprising wood pulp fluff having from 0% up to less than 10% of a polymeric material incorporated therewith.

18. The sanitary napkin of claim 15 wherein said wet crush width recovery is greater than about 80 percent.

19. The sanitary napkin of claim 15 wherein said wet crush width recovery is greater than about 90 percent.

20. The sanitary napkin of claim 15 wherein said acquisition orifice is longitudinally aligned along a central longitudinal axis of said sanitary napkin.

21. An absorbent article comprising:
    a) a liquid permeable cover;
    b) a liquid impermeable baffle;
    c) an absorbent core positioned between said cover and said baffle, said absorbent core having a first absorbent layer substantially comprising a fluff wood pulp and a second absorbent layer consisting essentially of a resilient cellulosic material wherein said absorbent core has a wet crush width recovery of greater than about 70 percent.

22. The absorbent article of claim 21 wherein said first absorbent layer has a density ranging from about 0.05 g/cc to about 0.22 g/cc and said second absorbent layer is uncreped through air dried cellulosic sheet.

23. The absorbent article of claim 21 wherein said second layer comprises one or more flat, resilient sheets consisting essentially of cellulosic material.

24. A sanitary napkin, comprising:
    a) a liquid permeable cover;
    b) a liquid impermeable baffle;
    c) an absorbent core positioned between said cover and said baffle, said absorbent core having a first absorbent layer, said first absorbent layer comprising a fluff wood pulp, said first absorbent layer having an inner boundary defining an acquisition orifice, said acquisition orifice extending through said first absorbent layer such that said second absorbent layer is in direct liquid contact with said permeable cover at said orifice, said acquisition orifice having a ratio of length to width greater than unity wherein said sanitary napkin, when crushed so that said sanitary napkin is approximately 40% of the pre-crushed dimensional width of said sanitary napkin, having a wet crush width recovery of greater than about 70 percent of the pre-crushed dimensional width of said sanitary napkin approximately 30 seconds after being allowed to recover.

25. The sanitary napkin of claim 24 wherein the size of said acquisition orifice comprises less than about 50% of the total top surface area of said first absorbent layer.

26. The sanitary napkin of claim 24 wherein the size of said acquisition orifice comprises less than about 25% of the total top surface area of said first absorbent layer.

27. The sanitary napkin of claim 24, said acquisition orifice being medially aligned along both the x-axis and the y-axis.

28. The sanitary napkin of claim 24, said second absorbent layer comprising 1 or more layers of material.

29. The sanitary napkin of claim 28, said baffle comprising a polyethylene film material.

30. The sanitary napkin of claim 28, said one or more layers of material comprising uncreped through air dried sheets of cellulosic material.

31. A sanitary napkin as in claim 24, said first absorbent layer comprising wood pulp fluff having from 0% up to less than 10% of a polymeric material incorporated therewith.

32. An absorbent article, comprising:
    a) a liquid permeable cover;
    b) a liquid impermeable baffle;
    c) an absorbent core positioned between said cover and said baffle, said absorbent core having a first absorbent layer and a second absorbent layer, said first absorbent layer substantially comprising a fluff wood pulp, said second absorbent layer consisting essentially of a resilient cellulosic material,
said absorbent article, when crushed so that said absorbent article is approximately 40% of the pre-crushed dimensional width of said absorbent article, having a wet crush width recovery of greater than about 70 percent of the pre-crushed dimensional width of said absorbent article approximately 30 seconds after being allowed to recover.

33. An absorbent article as in claim 32 wherein said wet crush width recovery is greater than about 80 percent.

34. An absorbent article as in claim 32, said first absorbent layer having an inner boundary defining an acquisition orifice, and wherein said wet crush width recovery is greater than about 90 percent.

35. An absorbent article as in claim 32, said first absorbent layer having an inner boundary defining an acquisition orifice, said acquisition orifice being longitudinally aligned along a central longitudinal axis of said sanitary napkin.

* * * * *

UNITED STATES PATENT AND TRADEMARK OFFICE
CERTIFICATE OF CORRECTION

PATENT NO. : 6,011,195
DATED : January 4, 2000
INVENTOR(S) : Laura J. Muhs, et al.

It is certified that error appears in the above-identified patent and that said Letters Patent is hereby corrected as shown below:

Column 4,
Line 7, delete "tom" and insert -- torn -- in place thereof.

Claim 1,
Line 1, delete "articles" and insert -- article -- in place thereof.

Claim 24,
Line 6, after the first occurrence of "layer" insert -- and a second absorbent layer --.

Signed and Sealed this

Sixteenth Day of October, 2001

Attest:

NICHOLAS P. GODICI
Attesting Officer    Acting Director of the United States Patent and Trademark Office